(12) United States Patent
Tamaazousti et al.

(10) Patent No.: US 10,497,136 B2
(45) Date of Patent: Dec. 3, 2019

(54) METHOD FOR PROCESSING IMAGES HAVING SPECULARITIES AND CORRESPONDING COMPUTER PROGRAM PRODUCT

(71) Applicant: COMMISSARIAT A L'ENERGIE ATOMIQUE ET AUX ENERGIES ALTERNATIVES, Paris (FR)

(72) Inventors: Mohamed Tamaazousti, Clamart (FR); Alexandre Morgand, Ivry-sur-seine (FR); Adrien Bartoli, Clermont-Ferrand (FR)

(73) Assignee: COMMISSARIAT A L'ENERGIE ATOMIQUE ET AUX ENERGIES ALTERNATIVES, Paris (FR)

( * ) Notice: Subject to any disclaimer, the term of this patent is extended or adjusted under 35 U.S.C. 154(b) by 115 days.

(21) Appl. No.: 15/574,475

(22) PCT Filed: Jun. 7, 2016

(86) PCT No.: PCT/EP2016/062877
§ 371 (c)(1),
(2) Date: Nov. 15, 2017

(87) PCT Pub. No.: WO2016/198389
PCT Pub. Date: Dec. 15, 2016

(65) Prior Publication Data
US 2018/0137635 A1 May 17, 2018

(30) Foreign Application Priority Data

Jun. 8, 2015 (FR) .................................... 15 55194

(51) Int. Cl.
*G06K 9/00* (2006.01)
*G06T 7/41* (2017.01)
(Continued)

(52) U.S. Cl.
CPC .................. *G06T 7/41* (2017.01); *G06T 7/73* (2017.01); *G06T 15/506* (2013.01); *G06T 15/83* (2013.01);
(Continued)

(58) Field of Classification Search
CPC ........ G06T 15/506; G06T 15/50; G01N 21/55
See application file for complete search history.

(56) References Cited

U.S. PATENT DOCUMENTS 3,922,093 A * 11/1975 Dandliker ............ G01B 11/303
250/222.1
5,028,138 A * 7/1991 Wolff ..................... G01B 11/24
356/364

(Continued)

OTHER PUBLICATIONS

Blinn, James F. "Models of light reflection for computer synthesized pictures." ACM SIGGRAPH computer graphics. vol. 11. No. 2. ACM, 1977.*

(Continued)

*Primary Examiner* — Li Liu
(74) *Attorney, Agent, or Firm* — Baker & Hostetler LLP

(57) ABSTRACT

A method for processing images of a scene including a surface made of a material of unknown reflectance comprises the following steps: from at least 3 different positions of an image sensor, the positions and corresponding orientations of the sensor known, acquiring images of the scene illuminated by a light source, each image containing specularity generated by reflection of the light source from the surface and depending on the position, the shape and the intensity of the light source and the reflectance of the material; in each image, detecting each specularity and for each specularity, estimating a conic approximating the specularity. It comprises constructing a quadric representing the position, intensity and shape of the light source and the reflectance of the material, on the basis of the conics, and of (Continued)

the position and orientation of the image sensor during the acquisition of the images containing the specularities respectively approximated by these conics.

14 Claims, 6 Drawing Sheets

(51) Int. Cl.
  *G06T 7/73* (2017.01)
  *G06T 15/50* (2011.01)
  *G06T 15/83* (2011.01)
(52) U.S. Cl.
  CPC ............ *G06T 2207/10016* (2013.01); *G06T 2207/30244* (2013.01)

(56) References Cited

U.S. PATENT DOCUMENTS

| | | | |
|---|---|---|---|
| 5,854,632 A * | 12/1998 | Steiner | G06T 15/506 345/426 |
| 2002/0152478 A1 * | 10/2002 | Stauder | G06T 15/50 725/143 |
| 2003/0011596 A1 | 1/2003 | Zhang et al. | |
| 2004/0227948 A1 * | 11/2004 | Debevec | G01N 21/55 356/445 |
| 2006/0244719 A1 | 11/2006 | Brigham et al. | |
| 2011/0116710 A1 * | 5/2011 | Garg | G06T 5/005 382/165 |
| 2012/0140233 A1 * | 6/2012 | Rockwell | G01N 21/55 356/445 |
| 2014/0307951 A1 | 10/2014 | Jin et al. | |
| 2015/0043806 A1 * | 2/2015 | Karsch | G06T 15/50 382/154 |
| 2017/0084075 A1 * | 3/2017 | Robert | G06T 15/506 |
| 2018/0023947 A1 * | 1/2018 | Meng | G01B 11/25 348/46 |

OTHER PUBLICATIONS

Cook, Robert L., and Kenneth E. Torrance. "A reflectance model for computer graphics." ACM Transactions on Graphics (TOG) 1.1 (1982): 7-24.*

Reyes, Leo, and Eduardo Bayro-Corrochano. "The projective reconstruction of points, lines, quadrics, plane conics and degenerate quadrics using uncalibrated cameras." Image and Vision Computing 23.8 (2005): 693-706.*

R. Woodham, "Gradient and curvature from the photometric-stereo method, including local confidence estimation," Journal of the Optical Society of America, vol. 11, No. 11, Nov. 1, 1994, pp. 3050, XP055004116.

Phong et al., "Illumination for computer generated pictures," Communications of the ACM, vol. 18, No. 6, 1975, pp. 311-317.

J. Van Maanen, "Seventeenth century instruments for drawing conic sections," The Mathematical Gazette, vol. 76, No. 476, Jul. 1992, pp. 222-230.

Cross et al., "Quadric reconstruction from dual-space geometry," International Conference on Computer Vision, ICCV, 1998.

A. Morgand et al., "Generic and real-time detection of specular reflections in images," 2014 International Conference on Computer Vision Theory and Applications (VISAPP), vol. 1, Jan. 5, 2014, pp. 274-282, XP032792001.

G. Gerules et al., "A survey of image processing techniques and statistics for ballistic specimens in forensics science," Sicence and Justice, vol. 53, No. 2, Aug. 11, 2012, pp. 236-250, XP028583351.

J. Jachnik et al., "Real-Time Surface Light-field Capture for Augmentation of Planar Specular Surface," ISMAR 2012.

M. Meilland et. al., "3D High Dynamic Range Dense Visual SLAM and its Application to Real-Time Object Re-Lighting," ISMAR 2013.

Lagger et. al., "Using Specularities to Recover Multiple Light Sources in the Presence of Texture," ICPR 2006.

B. Boom et. al., "Point Light Source Estimation based on Scenes Recorded by a RGB-D Camera," BMVC 2013, pp. 1-11.

S. Suzuki et al., "Topological structural analysis of digitized binary images by border following," Computer Vision, Graphics, and Image Processing, vol. 30, No. 1, 1985, pp. 32-46.

L.G. Khachiyan et al., "On the complexity of approximating the maximal inscribed ellipsoid for a polytope," Math. Programming, vol. 61, 1993, pp. 137-159.

A. W. Fitzgibbon et al., "A Buyer's Guide to Conic Fitting," BMVC 1995, pp. 513-522.

P. Sturm et al., "Conic fitting using the geometric distance," Asian Conference on Computer Vision, ACCV 2007.

* cited by examiner

METHOD FOR PROCESSING IMAGES HAVING SPECULARITIES AND CORRESPONDING COMPUTER PROGRAM PRODUCT

CROSS-REFERENCE TO RELATED APPLICATIONS

This application is a National Stage of International patent application PCT/EP2016/062877, filed on Jun. 7, 2016, which claims priority to foreign French patent application No. FR 1555194, filed on Jun. 8, 2015, the disclosures of which are incorporated by reference in their entirety.

FIELD OF THE INVENTION

The field of the invention is that of the processing of images containing specularities.

BACKGROUND

Reflection of light is observed when visible electromagnetic waves encounter a surface that does not absorb all of their radiative energy and repulses some thereof. When the imperfections of a surface are smaller than the wavelength of the incident light (this is the case of a mirror, for example), all of the light is reflected specularly (i.e. the angle of reflection of the light is equal to its angle of incidence). This effect causes, in images, specular spots, i.e. visible elements, on many materials.

In general, these specularities are not taken into account in machine-vision algorithms because these algorithms are highly dependent on viewpoint, on the materials present in the scene, on the settings of the video camera (exposure time, aperture) and on the geometry of the scene. These specularities are also dependent on the shape of the light source (bulb, fluorescent tube).

Now, these specularities are of major interest in various contexts. For augmented reality (AR) applications such as sales aids, the insertion of virtual elements into a real scene must be as natural as possible in order to allow an optimal user experience. Specifically, this insertion must be stable and include optical artefacts (the luminous context of the scene) such as specularities and shadows, elements that are essential for a realistic appearance.

Moreover, regarding the problem of real-time video-camera localization, current algorithms may be disrupted by specularities. Specifically, these algorithms are based on temporal tracking of primitives (generally points of interest). The latter may be completely or partially occulted by specularities. Current methods limit, to a certain extent, the problem by using robust estimation algorithms, which then consider these zones of the image to be noise. Nevertheless, for certain viewpoints, these specularities may saturate the video camera and cause the localization algorithms to fail. Ideally, these specularities should be considered as primitives in their own right, able to provide a great deal of additional information for reinforcing these localization algorithms.

These optical artefacts may also play an important role in the understanding and modelling of the behavior of light in a scene. Specifically, it is possible to deduce from these specularities the geometry of a surface on which they occur. These specularities may thus be used for quality-control applications in order to verify the integrity of a 3D surface during the manufacture of industrial parts.

The prediction of these optical artefacts and in particular the prediction of specularities is of major interest in the aforementioned applications. However, it is a difficult problem because specularities depend on the viewpoint of the observer, on the position, shape and intensity of the primary light sources and on the reflectance properties of the materials on which they occur.

The state-of-the-art regarding the estimation of light on the basis of images may be divided into two categories: the modelling of overall illumination and the reconstruction of primary sources.

Light is an essential element to the formation of an image. Specifically, the latter is the result of the interaction between light sources and objects of various materials for a given sensor (eye, video camera). This light is emitted by one or more light sources, which may be categorized into two categories:

Primary sources corresponding to bodies that produce the light that they emit. This category includes bodies having a very high temperature such as the sun, flames, incandescent embers or even a filament of an incandescent lamp.

Secondary or scattering sources corresponding to bodies that do not produce light but that redirect received light. Scattering is an effect in which a body, associated with a material, having received light, partially or completely redirects it in every direction. The amount of light scattered depends on the properties of the materials of the objects receiving the light. A scattering object is therefore a light source only when it is itself illuminated by a primary source or by another scattering object.

In their approach to modelling overall illumination, Jacknik et. al. propose in the publication "Real-Time Surface Light-field Capture for Augmentation of Planar Specular Surface" ISMAR 2012, an indirect reconstruction of overall illumination, taking the form of a map of the luminous environment generated on the basis of all the images of a video sequence. This reconstruction is used to achieve a realistic photo-finish after a phase of initialization on a planar surface made of a specular material. However, this method is limited because it makes no distinction between primary and secondary sources. Therefore, this method does not allow specularities from unknown viewpoints to be predicted.

The approach to estimating overall illumination of Meilland et. al. described in the publication "3D High Dynamic Range Dense Visual SLAM and its Application to Real-Time Object Re-Lighting" ISMAR 2013, presents a reconstruction of a primary (point) source achieved by directly filming light in the scene. However, this method is unsuitable for more complex types of lighting such as fluorescent tubes represented by a set of point sources. In addition, dynamic light (turned on, turned off) cannot be managed and, with regard to specularities, materials are not taken into account. Therefore, this method does not allow specularities from unknown viewpoints to be predicted.

The reconstruction of primary sources according to the method of Lagger et. al. described in the publication "Using Specularities to Recover Multiple Light Sources in the Presence of Texture" ICPR 2006, presents a reconstruction of the direction of the primary source on the basis of specularities on a moving object observed from a stationary viewpoint. This application is limited; specifically, as specularities depend on viewpoint, it is necessary to re-estimate them in each position. In addition, neither the position, nor the shape of the light source are estimated and material is not taken into account. Therefore, this method does not allow specularities from unknown viewpoints to be predicted.

The approach of Boom et. al. described in the publication "point Light Source Estimation based on Scenes Recorded by a RGB-D camera" BMVC 2013, details a method for estimating a primary light source that is considered to be point-like on the basis of a Lam bertian (nonreflective) surface, using a RGB-D (Red Green Blue-Depth) sensor. This approach only uses the diffuse component to estimate the point source, a synthesized appearance being compared with the actual scene in order to approach the actual scene as best as possible. However, this method is not suitable for real-time application, and cannot handle fluorescent tubes but only point sources, nor can it manage the presence of specularities (assumption of Lambertian surfaces). In addition, this method is limited to one light source and its shape is not estimated; furthermore, the specular component of materials is not taken into account. This method does not allow specularities from unknown viewpoints to be predicted.

Regarding the prediction of specularities, there is no known method.

Therefore, there remains to this day a need for a method for processing images containing specularities that optionally allows specularities from other viewpoints to be predicted.

SUMMARY OF THE INVENTION

The method for processing images including specularities according to the invention is based on the construction of a new model combining information on the light sources (intensity, position and shape), on the reflectance of the materials on which the specularities form, and possibly the roughness of the surface. From a technical point of view, a light source is reconstructed in the form of a generic 3D shape, here a quadric (sphere, ellipsoid, cylinder or even point). This empirical light-source model, which is symmetric with the real light source with respect to the surface, is reconstructed on the basis of images containing specularities that are observed on a planar surface of a given material, these images being obtained for given video-camera situations (or more generally given positions of an image sensor). Using a real-time detector of specularities and a video-camera localization method, the model is reconstructed in the form of a quadric that is able to represent not only a light bulb but also a fluorescent tube.

The constructed model allows a specularity in images, obtained from a new viewpoint, of the scene and including a surface made of this material to be predicted. Specifically, this model includes the position, intensity and shape of the light source and the reflectance of the material and possibly the roughness of the surface on which the specularity is present. The zone predicted for the specularity corresponds to a conic obtained by projection of the reconstructed quadric, for the given new video-camera situation.

More precisely, one subject of the invention is a method for processing images of a scene including a surface made of a material of unknown reflectance, which comprises the following steps:

from at least 3 known different orientations and positions of an image sensor, acquiring images of the scene illuminated by a light source, each image containing at least one specularity generated by reflection of the light source from said surface and depending on the position, on the shape, and on the intensity of the light source and on the reflectance of the material; and in each image, detecting each specularity.

It is mainly characterized in that it furthermore comprises the following steps:

for each specularity, estimating a conic approximating said specularity; and constructing a quadric representing the position, the intensity and the shape of the light source and the reflectance of the material, on the basis of the conics, and of the position and orientation of the image sensor during the acquisition of the images containing the specularities respectively approximated by these conics.

This method allows:

conjointly, information on the light sources and the properties of the materials of the scene to be included;

specular zones to be predicted for new viewpoints, for a given material;

a plurality of kinds of light to be managed (light bulbs and fluorescent strips);

a plurality of light sources to be estimated simultaneously;

the model, in quadric form, to be constantly refined with new viewpoints;

additional information to be given to the video-camera localization method;

the state of the light sources (turned on, turned off) to be updated;

any prior learning phase to be eliminated; and operation to be in real-time on-CPU.

Finally, a model is constructed combining information on the light source and the materials of the scene and that also allows specular zones to be predicted in real-time and precisely.

When the scene is illuminated by at least one other light source and each image contains at least one specularity generated by reflection of each other light source from said surface, the method furthermore comprises for each specularity:

temporal tracking of the specularity and matching said specularity, and therefore the conic approximating it, with a light source, and the step of constructing a quadric is carried out for each light source, on the basis of the conics matched with said light source, and of the position and orientation of the image sensor during the acquisition of the images containing the specularities respectively approximated by these conics.

It preferably furthermore includes the following steps:

for each specularity, minimizing the distance between the specularity and a conic resulting from projecting the quadric onto the image containing said specularity along an axis determined by the position and orientation of the sensor, in order to determine a new quadric; and iterating the preceding step until a preset stop criterion is reached, the new quadric resulting from the last iteration being a refined quadric representing the position, the intensity and the shape of the light source and the reflectance of the material.

It advantageously includes a step of choosing key images from the acquired images, depending on a predefined criterion of distribution of viewpoints of the sensor in the scene.

When a light source is a point light source, the corresponding quadric is a sphere; and, when it is an extended light source, the corresponding quadric is an ellipsoid.

It may also include a step of calculating a prediction of the position and shape of a conic (called the predicted conic) approximating a specularity formed on a surface made of a material of known normal, depending on a new position and a new orientation of said image sensor during the acquisition of a new image and on the projection of the quadric onto said new image.

When the material of the predicted specularity is the same as the material associated with the quadric, the size of the specularity is also predicted.

Scales of projection of the quadric being preset, the conic prediction calculation is advantageously carried out for each scale so as to obtain as many conics as scales, each conic corresponding to an intensity level of the predicted specularity.

According to one feature of the invention, it includes a step of correcting error in the position and orientation of the image sensor on the basis of a calculation of a discrepancy between a specularity present in the image associated with said position and orientation and a conic resulting from the projection of the quadric onto said image.

According to another feature of the invention, the different positions and orientations of the sensor are obtained using the same moving sensor or using a plurality of stationary sensors.

Another subject of the invention is a computer-program product, said computer program comprising code instructions allowing, on the basis of:

at least 3 known different orientations and positions of an image sensor, and images of the scene illuminated by a light source, which images are acquired by said image sensor, each image containing at least one specularity generated by reflection of the light source from said surface and dependent on the position, on the shape, and on the intensity of the light source and on the reflectance of the material, the following steps to be carried out when said program is executed on a computer:

in each image, detecting each specularity;

for each specularity, estimating a conic approximating said specularity; and constructing a quadric representing the position, the intensity and the shape of the light source and the reflectance of the material, on the basis of the conics, and of the position and orientation of the image sensor during the acquisition of the images containing the specularities respectively approximated by these conics.

BRIEF DESCRIPTION OF THE DRAWINGS

Other features and advantages of the invention will become apparent on reading the following detailed description, which is given by way of nonlimiting example and with reference to the appended drawings, in which.

Figure 1:
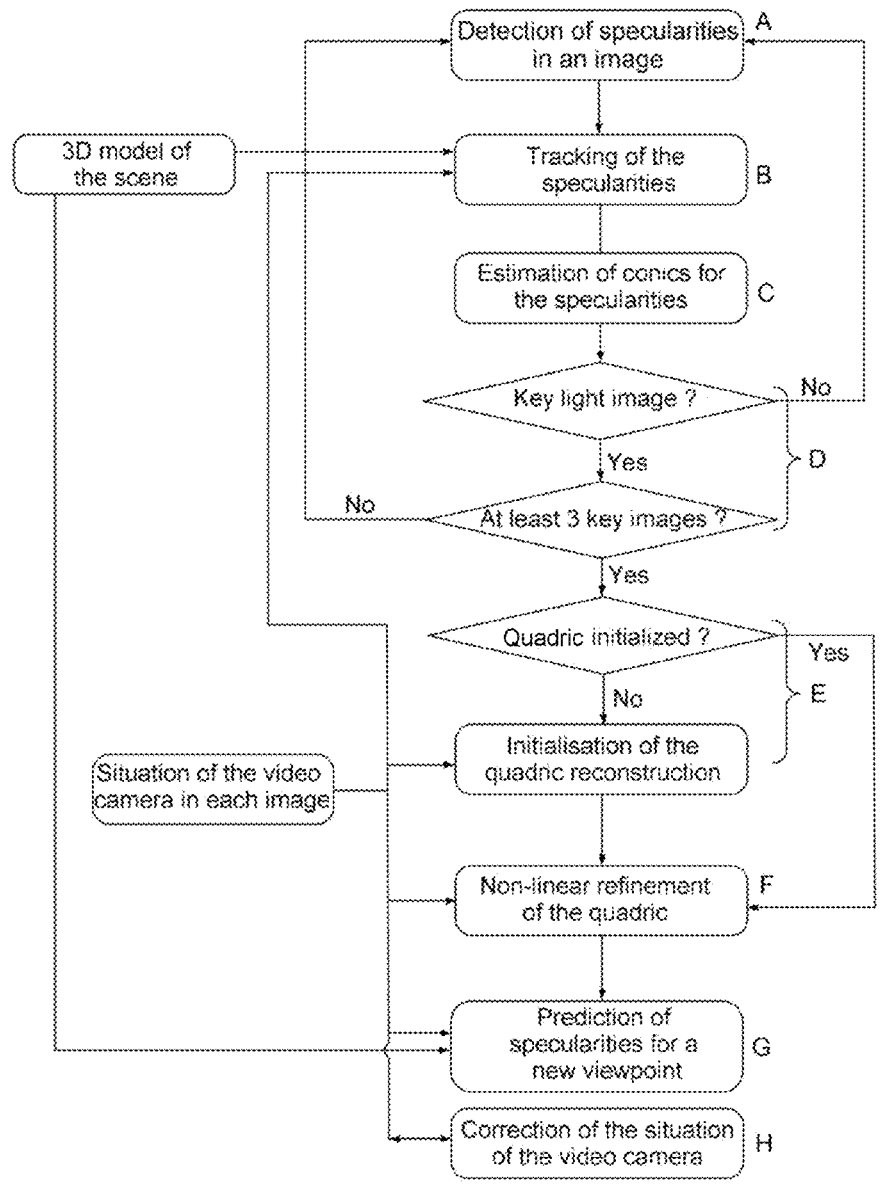
FIG. 1 shows a flowchart of the main steps of the method according to the invention.

From one figure to the next, elements that are the same have been referenced with the same references.

In the rest of the description, the expressions "top" and "bottom" are used with reference to the orientation of the described figures. Insofar as the image sensor may be positioned with other orientations, the directional terminology is given by way of illustration and is nonlimiting.

DETAILED DESCRIPTION

Knowledge of primary sources is essential for a better comprehension of the scene. To find these primary sources, a plurality of optical artefacts, such as shadows and specularities, that are available in the images, may be used.

1. Shadows correspond to zones occulted by an opaque object in a scene. These elements depend on the size of the occulting object and on its distance with respect to the primary sources. In addition, they are greatly influenced by the shape of the latter.

2. Specularities correspond to a total reflection of the primary source from a reflecting surface. These artefacts are dependent on the viewpoint and the materials on which they are observed.

A light sensor (eye, video camera) is sensitive to these optical artefacts. It is moreover the latter that generally assist a human being with interpretation of a scene (in particular information on depth, the coherence of the scene, etc.).

For machine-vision applications, light is therefore an essential element. Knowledge thereof may be advantageous in various applications:

For augmented-reality applications, realism is greatly dependent on the virtual insertion of these optical artefacts.

The algorithms used in the field of video-camera localization may be disrupted by the presence of specularities. Knowledge of these elements could improve these algorithms.

For the verification of properties of an object (geometry, materials) in the field of industrial inspection.

The method according to the invention is based on a method for constructing a virtual model allowing light sources of various shapes (light bulbs, fluorescent strips, etc.), the reflectance of a material and optionally the roughness of the surface to be modelled at the same time on the basis of specular reflections from a planar surface of this material; this planar surface may be curved. These specular reflections are sensitive to the properties of the light (shape, intensity, position) and to the properties of the material on which they are represented. Constructing a model on the basis of specularities also implies inclusion of the reflectance properties of the material. The construction of this virtual model will allow the specularities to be estimated via projection of the model for unknown viewpoints.

The light sources in question are stationary and are generally not very far from the surface presenting the specularities, as is the case for light sources located in the interior of a building or for an exterior streetlight. Nevertheless it will be noted that a source at infinity, such as the sun for example, may also be modelled by the method.

The images with specularities that are processed by the method according to the invention are acquired by a sensor the intrinsic parameters of which (focal length and central point) are known.

The situations of the image sensor are considered to be known for each image; a 3-D model of the scene is also known, in which only the normal to the plane (or the normals to the planes) on which the specularities are located is (are) used. These images may be obtained by a sensor moving along a known path, the images possibly themselves being obtained in video mode or in manual mode at times that are further apart, or by a plurality of stationary sensors located at various known locations.

The primitives used for the construction of the source model including the reflectance of the material correspond to the specular reflections in an image. These specularities are caused by the reflection of the light sources from a reflective (non-Lambertian) surface. It will be noted that the properties of the light source, such as its size, its position and its shape, influence the shape of the specularity on a surface. In addition, depending on the reflectance of the material, the size of these specularity is also modified. Knowledge of these elements is essential if the shape of the specularity is to be predictable for unknown viewpoints.

In the case of a planar surface, a specularity corresponds to the reflection of a light source with respect to a specular material (a perfectly specular material would correspond to a mirror). This property is important because it allows the number of light sources in a scene to be rapidly identified. In addition, tracking of these specularities allows the temporal state of the light sources associated with these artefacts to be observed.

On the basis of images obtained by a sensor in at least 3 different positions, the positions and corresponding orientations of the sensor being known, the construction of the model includes the steps shown in the flowchart of FIG. 1:

A. Detection of Specularities

This step consists in detecting specularities in an image. At the end of this step, the resulting image is a gray-scale image. These specularities are detected using the method described in the publication by the inventors "Generic and real-time detection of specular reflections in images" VISAPP, 2014. This approach is based on the observation that these specularities stand out more in the Hue-Saturation-Value (HSV) color space than, for example, in the RGB space. Specifically, specularities manifest themselves as high values in the Value channel and low values in the Saturation channel.

On the basis of this observation, this step is based on automatic thresholding of the Value and Saturation channels depending on the luminosity calculated from the image. In order to maximize the results, preprocessing (=before thresholding) and post-processing (=after thresholding) are implemented.

Depending on the luminosity calculated from the image, the preprocessing allows difficult images (due to overexposure of the video camera, an underexposure, or abrupt changes in lighting, etc.) to be anticipated. A contrast equalization is applied in order to make the specularities stand out more in the case of underexposure and in order to limit the saturation of the image in the case of overexposure. The image resulting from this preprocessing allows detection to be performed under better conditions but also allows images that it will be hard for methods for localizing the sensor in a video sequence to exploit to be anticipated. Specifically, the sensor (eye, video camera) is very sensitive to variations in the light that it receives.

The objective of the post-processing is to filter the various candidates resulting from the thresholding. After an equalization of the contrast, certain zones in the image remain falsely detected for an overexposed image in particular. Specifically, a white texture returns a large amount of light, this possibly leading to false detection, its light intensity being very high. To respond to this problem, a method for separating specular spots from ambiguous textures is implemented.

If the image is observed in the Value channel of the HSV, it is easy to observe, for each specularity, a gradual decrease in the intensity of the latter from its center. In order to exploit this criterion, the image is divided into k-regions of specular candidates. This segmentation is carried out using a conventional binary-image-segmentation method; for example, the method as described in the publication by Suzuki and Satoshi "Topological structural analysis of digitized binary images by border following" Computer Vision, Graphics, and Image Processing, 30(1): 32-46, 1985 may be used. The maximum circumscribed box is employed for each outline. Specifically, a specularity is nonuniform and is generally very fragmented. By using a maximum circumscribed box, these fragments are included in the calculation. Next, the threshold in the Value channel is gradually modified by one increment of unitary size in each iteration, the resulting variation in the area of these maximum circumscribed boxes being observed. If this variation is constant (equivalent to a slight and regular decrease in intensity), this candidate is considered to be a specularity. If the area decreases suddenly, this candidate probably represents a texture and has therefore been wrongly detected as being specular.

B. Tracking of the Specularities

Each specularity is associated with a light source. In order to track the state of the light sources in real-time, temporal tracking of each specularity is carried out on the basis of the outline of each thereof in successive images, in order to track variation in these outlines. For two successive images, if the preceding and current outline intersect, then the outline is updated and the specularity is tracked. If the outline disappears with respect to the preceding image, the specularity is no longer tracked (poorly detected outline, light that has been switched off). This tracking allows each specularity to be matched in real-time with a light source reflecting from the specular surface and that is the origin of this specularity from one image to the next. It is a question so to speak of indexing each specularity with an index that is specific to the light source that is the cause of said specularity.

In addition, this tracking allows specularities falsely detected in an image to be filtered. Specifically, white textures in the presence of strong light return light in large amounts, thereby possibly causing the image to saturate and leading to false detection of a specularity. However, for a plurality of images, the white texture remains stationary in the 3-D scene contrary to the specularity which, depending on the viewpoint of the sensor, will move in the scene. The principle of the filtering according to the invention is based on the dependency of the 3-D outline of the specularity, i.e. the outline obtained from the 3-D model of the scene, with respect to the position of the sensor. The warping method is used, which consists in calculating, for the specular candidates, the homography between two images from the situation (=position and orientation) of the sensor for these images. The candidate is considered to be a texture if its 3-D outline has not moved in the scene; it is considered to be a specularity if its 3-D outline has moved as illustrated in FIG.

3. The dotted outline of the candidate located in the center of the book has not moved in the scene between the right-hand image taken at a first viewpoint and the left-hand image taken at a second viewpoint and this candidate must be considered as to be a texture T; the solid-line outline of the candidate in the bottom right-hand corner of the book has moved in the scene between the right-hand image and the left-hand image and it is therefore a specularity S. To obtain this 3-D outline, each point of a 2-D outline is considered and ray tracing is carried out in the 3-D model of the scene on the basis of the situation of the sensor of the associated image. The intersection between the surface and these rays gives a 3-D outline that is analyzed for each image.

C. Estimation of Conics Representing the Specularities

According to the applicant, on a planar surface, an entire specularity (i.e. a specularity that is not cut-off) takes the form of an ellipse for various light sources (lightbulbs, fluorescent strips). A specularity more generally takes the form of a conic, but in the rest of the description an ellipse will be considered. The basis for this property is the physical model of reflection described by Phong et al. in the publication "Illumination for computer generated pictures" Communications of the ACM, 18(6):311-317, 1975, focusing only on the specular portion of the Phong equation, which gives the intensity of a 3-D point p as:

$$I_s(p) = i_s k_s \|\hat{R}\| \|\hat{V}\| \cos^n \alpha,$$

where $\hat{R}$ is the normalized direction of a perfectly reflected ray, $\hat{V}$ the normalized direction oriented towards the sensor, n the shininess (reflection coefficient of the light) of the material for which the ray cuts the plane, $k_s$ the ratio of reflection of the intensity of the light, $\alpha$ the angle between R and V and $i_s$ the intensity incident on the surface.

Let us consider a constant angle $\alpha$ and a plane $\pi$ of specular material. Thus, for this angle, the value of $I_s(p)$ is constant. On the basis of the Phong equation, it is possible to note that there is a maximum intensity at the point $p_0$ such that:

$$\exists p_0 \in \pi, I_s(p_0) = i_s k_s \Leftrightarrow \alpha = 0$$

According to Fermat's principle, the path of a light ray between two points is always the shortest possible path. The Snell-Descartes law of reflection may be derived from this principle: the angle $\theta_1$ between the normal N and the vector L, and the angle $\theta_2$ between the normal N and the vector R are equal. This principle implies that the incident plane containing N, L and R is orthogonal to $\pi$. This principle will be applied on the basis of two types of sources, point sources and extended sources.

For a point source such as a light bulb: in the Phong model, for a given angle $\alpha$, considering R to be the stationary arm and V (defined by the optical center P and p a point of the specularity on $\pi$) the arm of variable length, it is possible to draw a conic on the plane $\pi$ using a perfect virtual pair of compasses such as described for example in the publication by J. Van Maanen "Seventeenth century instruments for drawing conic sections" The Mathematical Gazette, pages 222-230, 1992.

It is interesting to note that the point $p_0$ is not located at the center of the ellipse of the specularity. It is possible to consider that there exists a cut-off angle $\alpha_{max}$ such that:

$$\exists \alpha_{max}, \alpha > \alpha_{max} \Leftrightarrow I_s(p) = 0$$

In addition, this cut-off angle implies that there exists a threshold $\tau$ such that:

$$\forall p \in S, I_s(p) > \tau, \text{ where } S \text{ is the set of the specular points.}$$

Figure 2:
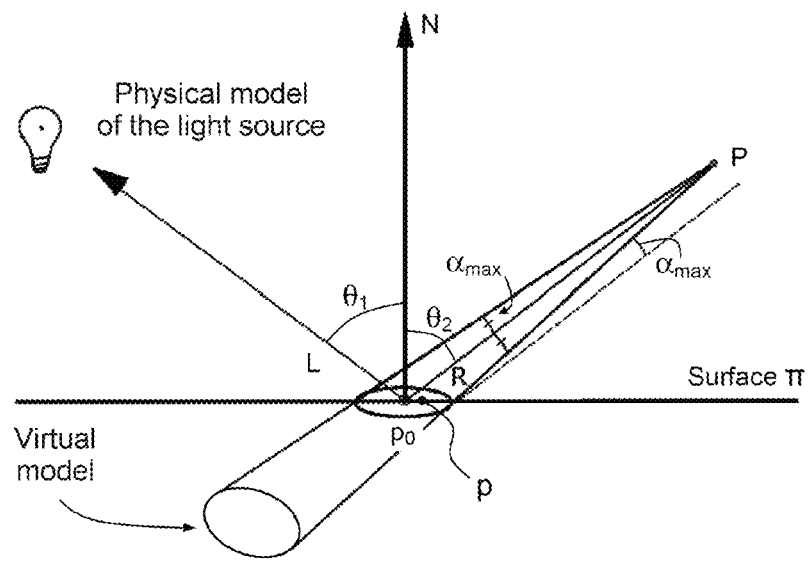
FIG. 2 schematically shows an example of specularity on a planar surface for an incident ray using the Phong model.
Figure 3:
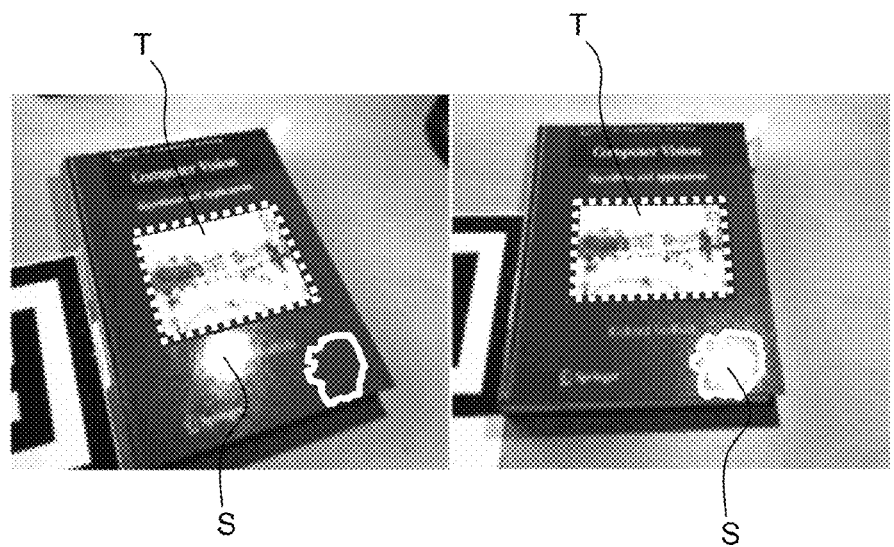
FIG. 3 illustrates an example of texture and specularity in two images taken from two different viewpoints.

Thus, in the Phong model, the applicant has proved that a point light source emits a specularity taking the form of a conic on the plane by using $\alpha_{max}$, $\tau$ and the perfect pair of compasses as illustrated in FIG. 2. Specifically, according to Fermat's principal, the path of a light ray is always the shortest. Thus, the plane formed by the incident and reflected ray (plane of incidence) is perpendicular to the plane $\pi$ (reflecting surface) which may be associated with the drawing surface of the perfect pair of compasses. If a specularity is entirely visible in the image on the plane $\pi$ then the specularity is of elliptical shape.

In the literature, for an extended source such as a fluorescent strip, the extended source is considered to be a discretized segment of point sources. It is known that these point sources produce specularities of elliptical shape on a planar surface of a reflective material. If this segment is considered to be infinitely discretized into point light sources, then it is possible to represent the specular spots by a maximum circumscribed ellipse. Thus, for an extended light source, the specularity obtained is also of elliptical shape.

Thus, for each type of light source, for a specular planar surface, it is possible to represent these (whole) specularities as ellipses.

Depending on the quality of the detection, two approaches for estimating ellipses on the basis of a gray-scale image delivered by the detector of specularities at the end of step A, are possible:

Maximum circumscribed ellipse estimation, which allows precise ellipses to be obtained for detections with little error as indicated in the publication L. G. Khachiyan, M. J. Todd, "On the complexity of approximating the maximal inscribed ellipsoid for a polytope", Math. Programming 61 (1993)137-159.

Fitted ellipse estimation, which allows potential errors due to the detection to be limited as indicated in the publication by A. W. Fitzgibbon, R. B. Fisher, et al. "A buyer's guide to conic fitting". DAI Research paper, 1996.

D. Choice of Key Images for the Light

For the sake of execution rapidity and precision in the estimation, the steps of constructing and optimizing the model are not carried out for each image but only for certain images called "key images". They are chosen by making a compromise between the quality of the specularities detected in the images and an angle criterion.

It is important to have key images corresponding to viewpoints distributed over the scene. On the basis of the reflected angles obtained beforehand, a threshold is set (for example experimentally) between the reflected angle of the current image and each angle of the already existing key images in order to obtain viewpoints that are far apart such that there is no intersection between the specularity detected in one key image and the specularity detected in the following key image. These key images may be obtained directly (without subsequent sorting) when for example the sensors used are stationary and have already been localized in locations that are sufficiently far apart to meet this far-apart-viewpoint criterion.

Figure 4:
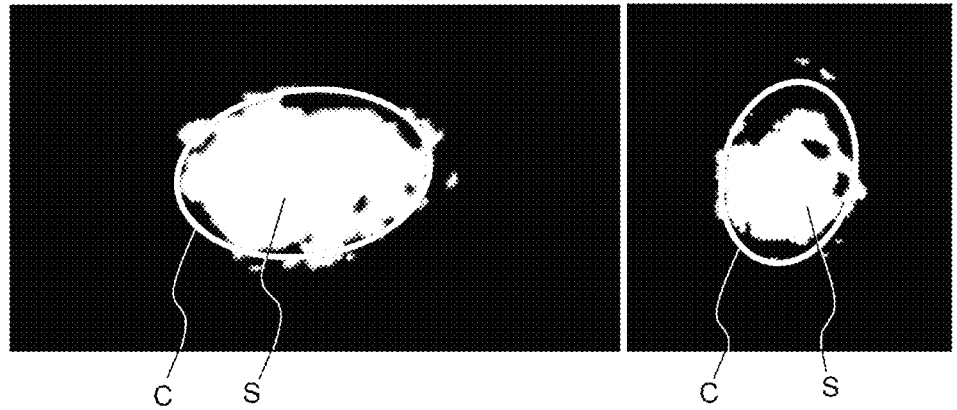
FIG. 4 illustrates two different approximations of a specularity by an ellipse.

All these criteria allow optimal viewpoints for the construction of the model to be obtained. Moreover, the granularity of a specular surface may influence the shape of the specularity. Therefore, it may be difficult to obtain an ellipse corresponding exactly to the specularity as illustrated in FIG. 4 in which it may be observed that the calculated ellipse C corresponds better to the outline of the specularity S in the left-hand image than in the right-hand image. The quality of the specularities is estimated by comparing the outline of the specularity obtained from the detector (=from the detection of step A) with the ellipse calculated for this specularity. This quality is estimated via a point/point distance between points on the outline of the specularity and the estimated ellipse. The Jaccard distance may also be used in order to compare the similarity between the area of the specularity and the area of the ellipse. These distances are detailed in the optimizing step.

E. Initialization

In the Phong model, the direction of the point light, and its intensity, must be estimated directly on the basis of a point source. According to the Phong formula, it is known that a specularity is influenced in size depending on the intensity of the light source. In practice, the calculation of this intensity is not trivial because the sensor is very sensitive to variations in light and the perceived intensity may vary.

It is proposed to reconstruct an empirical model of light sources as a virtual volume. This model includes the intensity and shape of the light source and the properties of the materials by reconstructing a quadric on the basis of conics estimated from the specularities associated with this light source.

Figure 5:
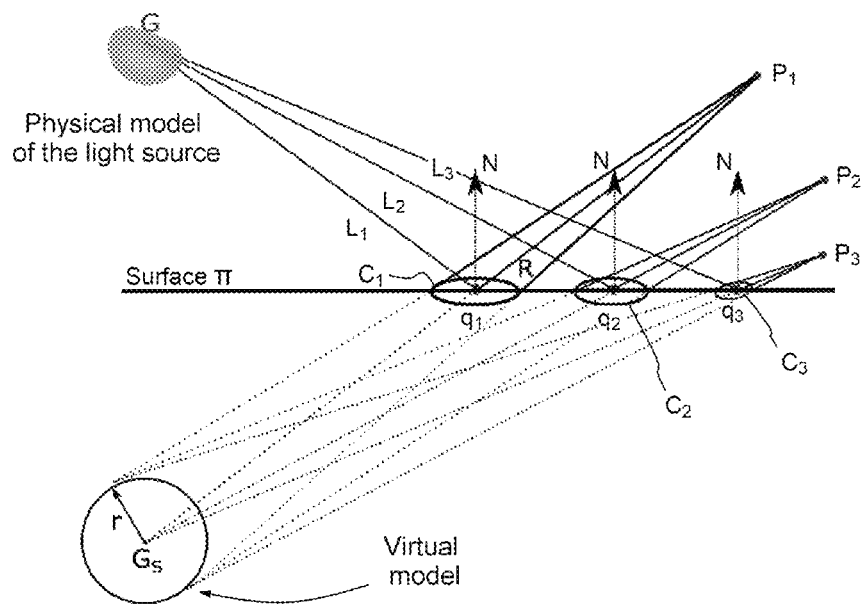
FIG. 5 schematically shows the links between a light source and a planar surface presenting specularities, and the corresponding virtual model according to the invention.

For a point source (lightbulb), the model according to the invention gives an equivalence to this point light source taking the form of a sphere as shown in FIG. 5. Specifically, for an omnidirectional point source at a fixed position G, there is a point $p_0 \in \pi$ such that the angle between the normal and the incident ray is equal to the angle between the normal between the reflected ray according to the Snell-Descartes principle. In the Phong model, $p_0$ is a point on the surface of maximum intensity. In FIG. 5, the intersection of the rays $P_1 q_1$, $P_2 q_2$ and $P_3 q_3$ corresponds to $G_s$ a point that is the reflection of G with respect to $\pi$; $P_1$, $P_2$, $P_3$ are the various positions of the sensor, $q_1$, $q_2$ and $q_3$ being the points of maximum intensity of the corresponding ellipses $C_1$, $C_2$, $C_3$. The point of maximum intensity is not necessarily at the center of the conic as may be seen in FIG. 8. Returning to FIG. 5, the applicant has demonstrated that, for each viewpoint, on a planar surface for a given specular material, a point source G produces a specularity of elliptical shape. The intersection of the various cones of revolution of vertices $P_1$, $P_2$ and $P_3$ (optical centers of the sensor) gives a sphere of radius r. This radius r is associated with an intensity and with the reflectance of the given material.

An analogy may be made between the model and a result due to the wave nature of light. Specifically, according to Huygen's principle, light propagates in the form of wavelets. A light source is considered to be isotropic, i.e. it emits light waves that propagate in rays in all directions: at each of the points of space close to the source and reached by the light wave, the state of the electromagnetic field oscillates (at the frequency of the source) between a maximum value and a minimum value. At a given time, all the points located at an identical distance from the source are in the same state: they are "in phase". The envelope of the points located at the same distance from the source makes a spherical shape in space. The surface of this sphere is called the wavefront, which may be considered to be a secondary source associated with the primary source.

Figure 6A:
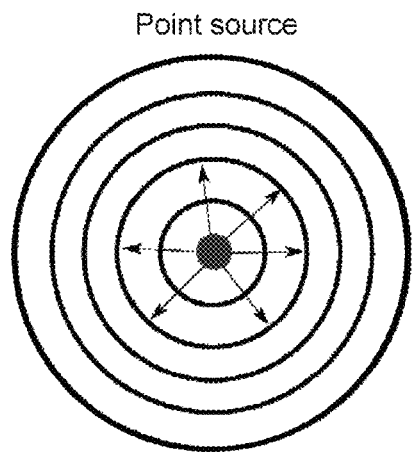
FIGS. 6a and 6b schematically show a point light source (left-hand image) and an extended source represented by a set of point sources on a segment generating on a planar surface specular spots circumscribed by an ellipse (right-hand image)

It may also be noted that for a given source, there are a plurality of wavefronts as shown in FIG. 6a in which each circle corresponds to a wavefront emitted by the central source in all directions. In the virtual model, it is possible to make an analogy with wavefronts by considering that, for each material, the specularity observed on its surface will embody a different wave-front level.

Figure 6B:
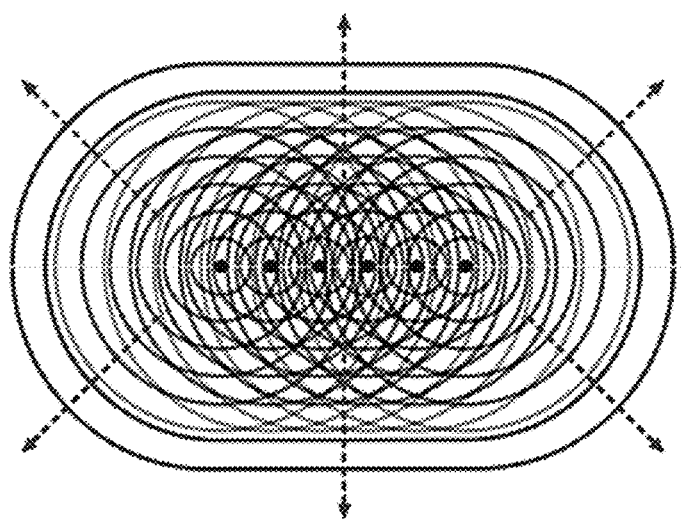

For an extended source such as a fluorescent strip:

In computer graphics, it is common to represent an extended source by a set of points (point sources). Thus a fluorescent strip is represented by a set of points distributed over a segment. For these points the waves, described by a sphere, are independent and originate from each point source. The interference of these spherical waves according to the Huygens-Fresnel principle will give a new wavefront the external envelope of which may be generalized by an ellipsoid as illustrated in FIG. 6b.

Thus, for an extended light source, the model according to the invention represents this source with an ellipsoid by analogy with the shape of the wavefront. These observations allow the virtual light-source model to be generalized using a quadric that may represent a sphere, an ellipsoid, a cylinder or even a point.

A few generalities on the construction of a quadric on the basis of conics will be recalled.

The procedure for initializing a quadric on the basis of conics will be presented after the formalism of conics and quadrics has been presented.

A quadric is a surface with 9 degrees of freedom which is represented by a symmetric matrix $Q \in \mathbb{R}^{4 \times 4}$ such that any point X on its surface satisfies the equation:

$$X^T Q X = 0,$$

where X is a 3-D point in homogenous coordinates.

The outline occulting a quadric in the image plane, for a given sensor situation, corresponds to a conic that is an outline with 5 degrees of freedom and that is represented by a symmetric matrix $C \in \mathbb{R}^{3 \times 3}$ such that any point x on its outline meets the constraint:

$$x^T C x = 0,$$

where x is a 2-D point in homogenous coordinates.

In order to express C as a function of Q, the dual space is used instead of the primal space because the relationship between C and Q is not direct in the primal space. Using the dual space for the 3-D reconstruction makes it possible to dispense with depth information. In this space, the conics are represented using lines I such that:

$$I^T C^* I = 0,$$

where $C^*$ is the dual conic.

For a dual quadric $Q^*$, a representation of the plane $\pi$ described by the following relationship is used:

$$\pi^T Q^* \pi = 0.$$

In the dual space, it is possible to use, to within a scale factor, the following relationship:

$$C^* \sim P Q^* P^T,$$

with $Q^* = \mathrm{adj}(Q)$ and $C^* = \mathrm{adj}(C)$, where adj is the adjucate (=the transposed cofactor matrix).

The method described in the publication Cross et al. "Quadric reconstruction from dual-space geometry" in International Conference on Computer Vision, ICCV, 1998, is used, which allows $Q^*$ to be reconstructed by converting the relationship between $Q^*$ and $C^*$ into a linear system. By vectorising Q, P and C into the form $Q_v$, B and $C_v$, for n viewpoints with $n \geq 3$ we can reconstruct a system by using specular reflections taking the form of conics C and the model of the light source taking the form of Q:

$$Mw = 0 \iff \begin{pmatrix} B_1 & -C^*_{1,v} & 0 & \cdots & 0 \\ B_2 & 0 & -C^*_{2,v} & & 0 \\ \vdots & 0 & 0 & \ddots & \vdots \\ B_n & 0 & 0 & \cdots & -C^*_{n,v} \end{pmatrix} \begin{pmatrix} Q^*_v \\ \alpha_1 \\ \alpha_2 \\ \vdots \\ \alpha_n \end{pmatrix} = 0,$$

With the matrix $B_i \in \mathbb{R}^{6 \times 10}$.

The solution to this system is calculated on the basis of a singular-value decomposition (SVD) of M. It will be noted that $\alpha_1$ corresponds to a scale factor such that:

$$\alpha_i C^*_{i,v} = B_i Q^*_{i,v}$$

for the viewpoint i.

This procedure is illustrated in FIG. 5 for three viewpoints; the sphere of radius r is constructed on the basis of the three ellipses respectively associated with the three specularities. The sphere of radius r includes the intensity of the light source and properties of the material of the surface on which the specularities are present. The cones of revolution indicated by the dotted lines in the figure and respectively issued from the points $P_i$, are not explicitly calculated to determine the quadric.

This step is carried out for each indexed light source. Tracking specularities in the images allows a first model to be constructed for each light source, independently. At the end of this step, quadrics that each represent one light source will have been constructed.

F. Optimization

This phase allows the construction of the light-source model to be refined (for each of the light sources) via a minimization, for the various viewpoints, of the distance between the projections of the quadric and the outlines of the specularities of each image. Thus, the optimization is based on the minimization, for all the light sources, of a non-linear cost function that allows the ellipses generated from the projections to be made to correspond as best as possible to the corresponding specularities in the images. This cost function may be calculated differently depending on the chosen distance.

F.1. Jaccard Distance

Figures 7A, 7B:
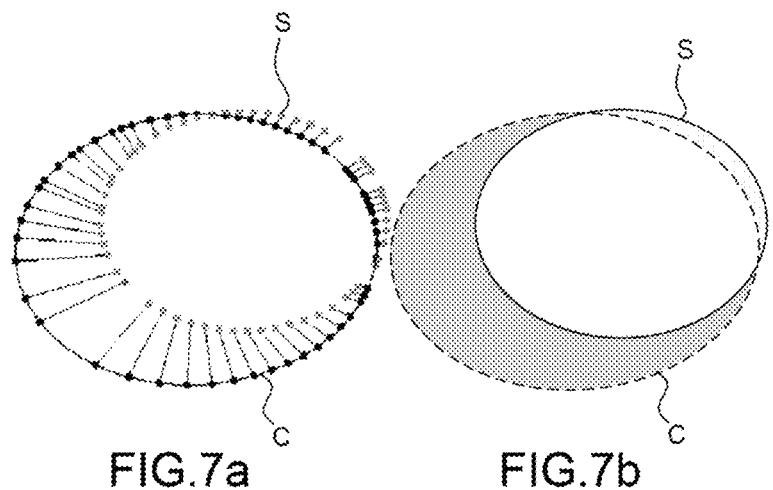
FIGS. 7a and 7b schematically show two examples of distances between a specularity and a corresponding ellipse, with the point/point distance (FIG. 7a) and the Jaccard distance (FIG. 7b)

The Jaccard distance quantifies the similarity between two sets (area of the specularity S bounded by a solid line and area of the projected conic (ellipse in our example) bounded by a dashed line) as shown in FIG. 7b in which each of the two areas and their intersection may be seen, and is given by the equation:

$$J(C, S) = \frac{|C \cap S|}{|C \cup S|}$$

where C is a conic and S a specularity detected in an image.

Jaccard Cost Function:

The objective of this cost function is to maximize, for all the viewpoints, the similarity between the area of the specularity and the conic generated by projecting the quadric.

The cost function is described by the equation:

$$\underset{Q_k}{\mathrm{Max}} \sum_{i=1}^{n} J(C'_{i,k}, S_{i,k})$$

where $S_i$ are the specular pixels in the image and $C'_i$ is the conic for the image of index i and the light source of index k.

F.2. Point/Point Distance for the Cost Function

A point/conic distance between the outline of a specularity and that of its associated projected conic is not usable as such. Specifically, calculating the distance between a point and a conic involves calculating a root of order 4 of a polynomial, this being expensive in terms of computing time and not allowing analytical derivatives to be obtained.

The desired solution is to obtain a parameterization of the conic into points respectively associated with each outline point, i.e. similar to the approach described in the publication P. Sturm and P. Gargallo "Conic fitting using the geometric distance" In Asian Conference on Computer Vision, ACCV.2007.

Various cost-function calculations may be used to calculate this point/point distance, which is illustrated in FIG. 7a. Two thereof are presented.

Cost Function with Point/Point Distance

The objective of this cost function is to minimize all the Euclidean distances "d" between the projections $C_i$ of the quadric Q for a viewpoint of index i as a function of Q as shown in FIG. 7a. This distance is given by the equation:

$$\underset{Q_k}{\min} \sum_{i=1}^{n} \sum_{j=1}^{m_i} d(q'_{i,j}, q_{i,j,k})$$

where $q'_{i,j,k}$ is the point (represented by a solid circle) of index j of the outline of the specularity S of index i and $q_{i,j,k}$ is the point obtained from the parameterization of the conic C (represented by a cross) of index i. This operation is carried out for the light source k.

In the case of the cost function for the point/point distance, the conic must be discretized in each iteration.

Another solution is to use latent variables in order to preserve the same pairs of points (specularity/conic) instead of recalculating these pairs in each iteration. However, the constraint to be met is to have latent variables able to vary only on the outline of its associated conic. Now, a point of a conic is defined by the relationship: $x^T Cx = 0$, where C is a conic and x a 2-D point in homogenous coordinates.

Thus the cost function may be re-written in the form:

$$\begin{cases} \underset{Q_k, q_{1,1}, \ldots, q_{n,m_i}}{\min} \sum_{i=1}^{n} \sum_{j=1}^{m_i} d(q'_{i,j,k}, q_{i,j,k}) \\ \text{subject to} \qquad q'_{i,j,k} C_j q'^T_{i,j,k} = 0 \end{cases},$$

It will be noted that the quadric to be refined is in general represented by a matrix $Q \in \mathbb{R}^{4 \times 4}$ such that: $X^T QX = 0$, where X is a 3-D point belonging to the surface of the quadric.

This quadric may also be represented parametrically (center of the quadric, scale of each axis, rotation about each axis).

At the end of this step, refined quadrics that each represent one light-source model will have been constructed. When a plurality of quadrics coincide, they then represent a model of the same light source.

G. Specularity Prediction:

Once the model has been constructed and refined, it is possible to directly project this model onto the image plane $\pi_i$ in order to predict the specularity Sp in a current new image acquired using the sensor with a new but known orientation and position P and with the same material. This function is particularly useful in the field of augmented reality. The projection of the (modelled) quadric onto this new image gives a conic bounding the zone predicted for the specularity.

Although the model is applicable for a given material, it is possible to estimate a specularity, defined to within a factor, for another planar surface of a specular material different from that of the model but of known normal: the center of the projected conic indicates the center of the zone predicted for the specularity, the dimensions of the specularity being those of the conic to within a scale factor. It will also be noted that for complex objects, by discretization of the outline occulting the quadric for an unknown viewpoint, it is possible, by ray tracing, to predict the outline of the specularity on this object.

Figure 8:
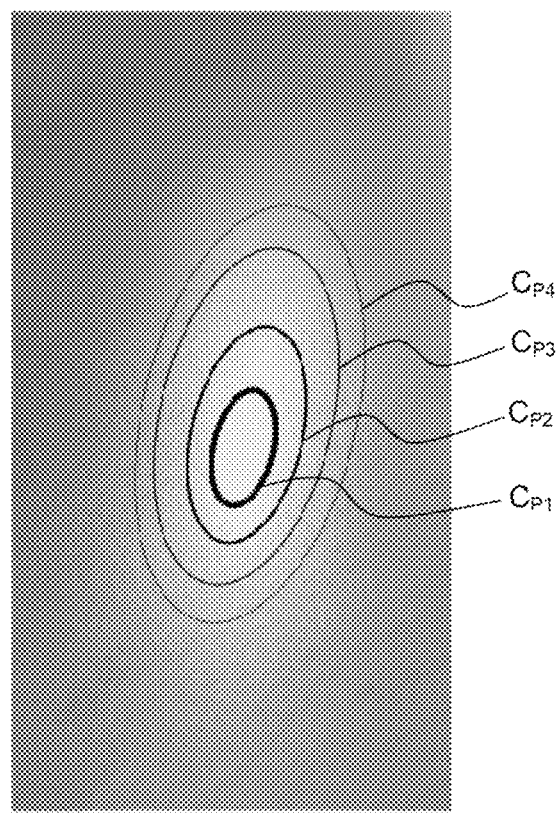
FIG. 8 illustrates a plurality of intensity levels of a specularity, respectively represented by conics.
Figure 9:
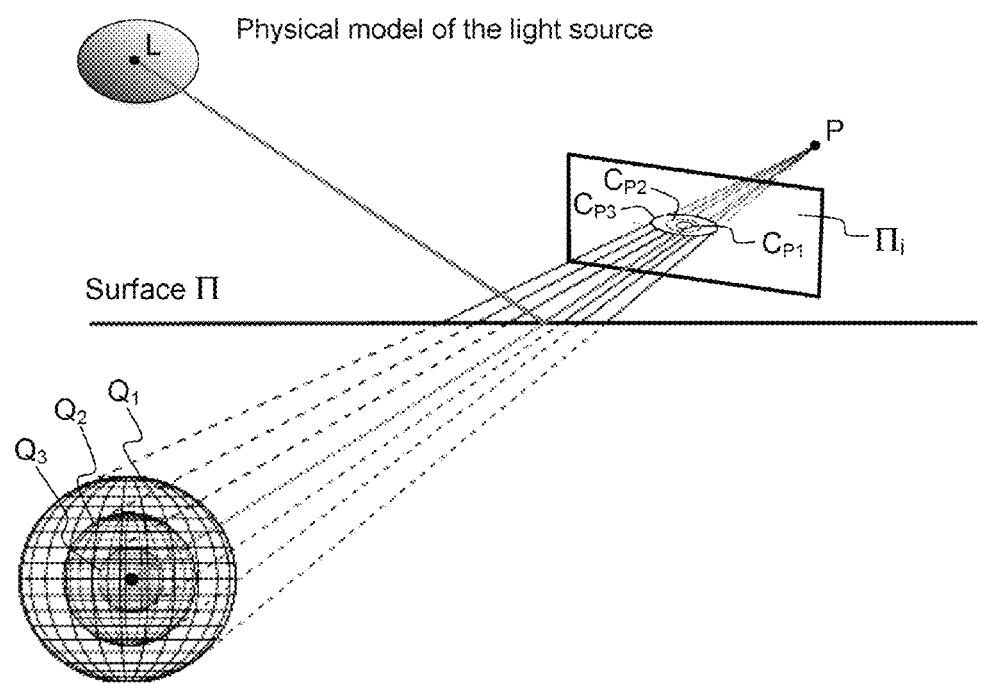
FIG. 9 schematically shows a plurality of concentric quadrics respectively corresponding to a plurality of scales, each projected quadric being a conic associated with one intensity level of the predicted specularity.

Generally, a specularity possesses various intensity levels. Specifically, a specularity possesses a zone of maximum intensity and its intensity decreases with distance from this zone. In our model, the various intensity levels are all represented by conics as shown in FIG. 8 with 4 conics Cp1, Cp2, Cp3, Cp4 (and therefore 4 intensity levels). It is important to note that the latter are not concentric, as may be seen in this figure. The specularity-predicting method allows the maximum circumscribed outline of the specularity Sp to be estimated on the basis of the strict projection of the quadric, and the various intensity levels of the specularity to be estimated by projecting quadrics of various scales, as shown in FIG. 9 for 3 quadric scales. The 3 concentric quadrics $Q_1, Q_2, Q_3$ (illustrating 3 quadric scales) projected onto the image plane $\pi_i$ produce 3 (predicted) conics Cp1, Cp2, Cp3 corresponding to 3 intensity levels of the predicted specularity Sp. Therefore, our model also allows the zone of maximum intensity of the specularity to be predicted.

H. Correction of the Position and Orientation of the Sensor

When specularity is predicted on the basis of the constructed and optionally refined model, it is also possible to correct possible errors in sensor position and orientation on the basis of a calculation of a discrepancy between a specularity present in the image associated with said position and said orientation and a conic resulting from projecting the modelled quadric onto said image. In practice, this step is carried out using one of the aforementioned cost functions with the position and orientation of the video camera as minimization parameter; this cost function is calculated using the outline of the detected specularity and used to construct the model of the source and the outline of the predicted specularity.

The method has been implemented (detection with temporal tracking of specularities, quadric reconstruction and nonlinear refinement) and validated quantitatively and quantitatively on synthetic sequences and on real sequences. These tests were carried out in complex environments with various light sources (lightbulbs and fluorescent lights) for objects (examples: table, kitchen, board, book, etc.) made of different materials (steel, plastic, varnished wood, china). The realized sequences highlight the precision of the method regarding the prediction of specular spots from viewpoints not used for the reconstruction. In addition, the video stream was treated in real-time (30 images per second on average) with the proposed approach.

For all the applications of augmented reality, sensor localization, surface quality control, etc., machine vision using a method according to the invention therefore offers an inexpensive, practical and non-invasive solution.

This method for processing images containing specularities may be implemented on the basis of images obtained by one movable sensor (or a plurality of stationary sensors) located in a scene, and on the basis of a 3-D geometric model of this scene.

This method may in particular be implemented using a computer-program product, this computer program comprising code instructions allowing the steps of the method for processing images acquired by the sensor to be performed. It is then stored on a medium that is readable by computer, such as for example a computer that has access to a 3-D geometric model of the scene and the positions and orientations of the sensor. The medium may be electronic, magnetic, optical, electromagnetic or be a storage medium read using infrared light. Such media are for example semiconductor memories (random-access memory (RAM) or read-only memory (ROM)), tapes, floppy disks or magnetic or optical (Compact Disk-Read Only Memory (CD-ROM), Compact Disk-Read/Write (CD-R/W) or DVD) disks.

Although the invention has been described with reference to particular embodiments, it will be obvious that it is in no way limited thereto and that it comprises any technical equivalent of the described means and combinations thereof if the latter fall within the scope of the invention.

The invention claimed is:

1. A method for processing images of a scene including a surface made of a material of unknown reflectance, the method comprising the following steps:
   from at least 3 different positions of an image sensor, the positions and corresponding orientations of the sensor being known, acquiring images of the scene illuminated by a light source, each image containing at least one specularity generated by reflection of the light source from said surface and depending on the position of the light source, on the shape of the light source and on the intensity of the light source and on the reflectance of the material;
   in each image, detecting each specularity; and
   for each specularity, estimating a conic approximating said specularity;
   constructing a quadric representing the position of the light source, the intensity of the light source, the shape of the light source, the reflectance of the material, on the basis of the conics, the position, and the orientation of the image sensor during the acquisition of the images containing the specularities respectively approximated by these conics.

2. The image-processing method as claimed in claim 1, the surface having an unknown roughness, the quadric also represents the roughness of the surface.

3. The image-processing method as claimed in claim 1, wherein the scene is illuminated by at least one other light source, each image containing at least one specularity generated by reflection of the at least one other light source from said surface, and further comprising for each specularity:
   temporal tracking of the specularity and
   matching said specularity, and therefore the conic approximating it, with a light source,
   and wherein the step of constructing a quadric is carried out for each light source, on the basis of the conics matched with said light source, and of the position and orientation of the image sensors during the acquisition of the images containing the specularities respectively approximated by these conics.

4. The image-processing method as claimed in claim 1, further comprising the following steps:
for each specularity, minimizing the distance between the specularity and a conic resulting from projecting the quadric onto the image containing said specularity along an axis determined by the position and orientation of the sensor, in order to determine a new quadric; and
iterating the preceding step until a preset stop criterion is reached, the new quadric resulting from the last iteration being a refined quadric.

5. The image-processing method as claimed in claim 1, comprising a step of choosing key images from the acquired images, depending on a predefined criterion of distribution of viewpoints of the sensor in the scene with respect to the light source.

6. The image-processing method as claimed in claim 1, wherein the light source is a point source and wherein the corresponding quadric is a sphere.

7. The image-processing method as claimed in claim 1, wherein the light source is an extended source and wherein the corresponding quadric is an ellipsoid.

8. The image-processing method as claimed in claim 1, comprising a step of calculating a prediction of the position and shape of a conic called the predicted conic approximating a specularity formed on a surface made of a material of known normal, depending on a new position and a new orientation of said image sensor during the acquisition of a new image and on the projection of the quadric onto said new image.

9. The image-processing method as claimed in claim 8, wherein quadric scales being preset, the conic prediction calculation is carried out for each scale so as to obtain as many conics as scales, each conic corresponding to an intensity level of the predicted specularity.

10. The image-processing method as claimed in claim 8, wherein the material of the predicted specularity is the same as the material associated with the quadric, and wherein the size of the predicted specularity is also predicted.

11. The image-processing method as claimed in claim 1, comprising a step of correcting error in the position and orientation of the image sensor on the basis of a calculation of a discrepancy between a specularity present in the image associated with said position and orientation and a conic resulting from the projection of the quadric onto said image.

12. The image-processing method as claimed in claim 1, wherein the different positions and orientations of the image sensor are obtained using the same moving image sensor or using a plurality of stationary image sensors.

13. A computer-program, comprising instructions stored on a tangible non-transitory storage medium for executing, on the basis of:
at least 3 different positions of an image sensor, the positions and corresponding orientations of the sensor being known, and
images of a scene including a surface, made of a material of unknown reflectance, illuminated by a light source, which images are acquired by said image sensor, each image containing at least one specularity generated by reflection of the light source from said surface and dependent on the position of the light source, on the shape of the light source, on the intensity of the light source and on the reflectance of the material,
the following steps to be carried out when said program is executed on a computer:
in each image, detecting each specularity;
for each specularity, estimating a conic approximating said specularity; and
constructing a quadric representing the position of the light source, the intensity of the light source, the shape of the light source, the reflectance of the material, on the basis of the conics, the position, and the orientation of the image sensor during the acquisition of the images containing the specularities respectively approximated by these conics.

14. A computer-program as claimed in claim 13, wherein the surface having an unknown roughness, the quadric also represents the roughness of the surface.

* * * * *